(12) United States Patent
Dull et al.

(10) Patent No.: US 8,461,344 B2
(45) Date of Patent: Jun. 11, 2013

(54) POLYMORPH FORMS OF (2S)-(4E)-N-METHYL-5-[3-(5-ISOPROPDXYPYRIDIN)YL]-4-PENTEN-2-AMINE

(75) Inventors: Gary M. Dull, Lewisville, NC (US); Julio A. Munoz, Walnut Cove, NC (US)

(73) Assignee: Targacept, Inc., Winston-Salem, NC (US)

( * ) Notice: Subject to any disclaimer, the term of this patent is extended or adjusted under 35 U.S.C. 154(b) by 1057 days.

(21) Appl. No.: 11/745,682

(22) Filed: May 8, 2007

(65) Prior Publication Data

US 2007/0265314 A1 Nov. 15, 2007

Related U.S. Application Data

(60) Provisional application No. 60/746,821, filed on May 9, 2006.

(51) Int. Cl.
*C07D 213/65* (2006.01)
*A61K 31/44* (2006.01)

(52) U.S. Cl.
USPC .......................................... 546/300; 514/351

(58) Field of Classification Search
USPC .......................................... 514/351; 546/300
See application file for complete search history.

(56) References Cited

U.S. PATENT DOCUMENTS

| | | | |
|---|---|---|---|
| 4,192,946 A | 3/1980 | Clauson-Kaas et al. | |
| 4,487,607 A | 12/1984 | Rose et al. | |
| 4,582,823 A | 4/1986 | Heffner et al. | |
| 4,922,901 A | 5/1990 | Brooks et al. | |
| 5,013,753 A | 5/1991 | Casagrande et al. | |
| 5,073,547 A | 12/1991 | Casagrande et al. | |
| 5,187,166 A | 2/1993 | Kikuchi et al. | |
| 5,212,188 A | 5/1993 | Caldwell et al. | |
| 5,583,140 A | 12/1996 | Bencherif et al. | |
| 5,597,919 A | 1/1997 | Dull et al. | |
| 5,604,231 A | 2/1997 | Smith et al. | |
| 5,616,707 A | 4/1997 | Crooks et al. | |
| 5,616,716 A | 4/1997 | Dull et al. | |
| 5,663,356 A | 9/1997 | Ruecroft et al. | |
| 5,672,601 A | 9/1997 | Cignarella | |
| 5,726,316 A | 3/1998 | Crooks et al. | |
| 5,811,442 A | 9/1998 | Bencherif et al. | |
| 5,852,041 A | 12/1998 | Cosford et al. | |
| 5,861,423 A | 1/1999 | Caldwell et al. | |
| 6,232,316 B1 | 5/2001 | Dull et al. | |
| 6,337,351 B1 | 1/2002 | Dull et al. | |
| 6,432,954 B1 | 8/2002 | Dull et al. | |
| 6,492,399 B1 | 12/2002 | Dull et al. | |
| 6,599,897 B1 | 7/2003 | Brown | |
| 6,603,011 B1 | 8/2003 | Caldwell et al. | |
| 6,632,823 B1 | 10/2003 | Vernier et al. | |
| 6,743,812 B1 | 6/2004 | Dull | |
| 6,958,399 B2 | 10/2005 | Caldwell et al. | |
| 7,459,469 B2 * | 12/2008 | Munoz et al. | 514/351 |
| 2002/0016460 A1 | 2/2002 | Snow et al. | |
| 2002/0052497 A1 | 5/2002 | Caldwell et al. | |
| 2003/0069272 A1 | 4/2003 | Yerxa et al. | |
| 2004/0044023 A1 | 3/2004 | Cantillon et al. | |
| 2004/0067974 A1 | 4/2004 | Czollner et al. | |
| 2005/0203130 A1 | 9/2005 | Buntinx | |
| 2006/0024358 A1 | 2/2006 | Santini et al. | |
| 2006/0062838 A1 | 3/2006 | DiPierro et al. | |
| 2006/0122237 A1 | 6/2006 | Munoz et al. | |
| 2006/0122238 A1 | 6/2006 | Dull et al. | |
| 2006/0159768 A1 | 7/2006 | Brown | |
| 2007/0265314 A1 | 11/2007 | Dull et al. | |
| 2008/0085888 A1 | 4/2008 | Breining et al. | |
| 2008/0249142 A1 * | 10/2008 | Dull et al. | 514/357 |
| 2009/0062321 A1 * | 3/2009 | Munoz et al. | 514/277 |

FOREIGN PATENT DOCUMENTS

| | | |
|---|---|---|
| EP | 0297858 | 1/1989 |
| EP | 0516409 | 12/1992 |
| GB | 2295387 | 5/1996 |
| JP | 2002518373 | 6/2002 |
| JP | 2008519768 | 6/2008 |
| WO | 9212122 | 7/1992 |
| WO | 9408992 | 4/1994 |
| WO | 9534555 | 12/1995 |
| WO | 9631475 | 10/1996 |
| WO | 9640682 | 12/1996 |
| WO | 9740011 | 10/1997 |
| WO | 9850367 | 11/1998 |
| WO | 9921834 | 5/1999 |
| WO | 9965876 | 12/1999 |
| WO | 0007600 | 2/2000 |
| WO | 2004/031151 A1 | 8/2000 |
| WO | 0075110 | 12/2000 |
| WO | 0117943 | 3/2001 |
| WO | 0178735 | 10/2001 |
| WO | 0205801 A2 | 1/2002 |

(Continued)

OTHER PUBLICATIONS

Gould "Salt selection for basic drugs," International Journal of Pharmaceutics (1986) 33:201-217.
70012732, JP, Daiichi Seiyaku.
Grottick et al., "Effect of subtype selective nicotinic compounds on attention as assessed by the five-choice serial reaction time task," Behav Brain Res. (2000) 117:197-208.
de Costa et al., "Synthesis and biological evaluation of conformationally restricted 2-(1-pyrrolidinyl)-N-[2-(3,4-dichlorophenypethy1]-N-methylethylenediamines as sigma receptor ligands. 1. Pyrrolidine, piperidine, homopiperidine, and tetrahydroisoquinoline classes," J med Chem (1992) 35(23):4334-4343.
Koller et al., "The Preparation of Substituted Hydroxyphenyl-pyridyl-ethanols and -Hydroxyphenyl—methylpyridineethanols by the Condensation of 2-, 3-, or 4-Picolyllithium with Select Hydroxy-benzaldehydes and 4-Hydroxyacetophenone," Synthetic Communications (1995) 25(19):2963-2974.

(Continued)

Primary Examiner — David K O Dell
(74) Attorney, Agent, or Firm — Amy H. Fix

(57) ABSTRACT

Polymorph forms of (2S)-(4E)-N-methyl-5-[3-(5-isopropoxypyridin)yl]-4-penten-2-amine p-hydroxybenzoate, and methods for their preparation, pharmaceutical composition containing said polymorph(s) and use, are disclosed. The polymorphs can be administered to patients susceptible to or suffering from conditions and disorders, such as central nervous system disorders, to treat and/or prevent such disorders.

6 Claims, No Drawings

FOREIGN PATENT DOCUMENTS

| | | |
|---|---|---|
| WO | 02078693 | 10/2002 |
| WO | 03051302 | 6/2003 |
| WO | 03082205 | 10/2003 |
| WO | 2005/072742 A1 | 4/2004 |
| WO | 2005063296 A2 | 7/2005 |
| WO | 00/45846 A1 | 8/2005 |
| WO | 2005105729 | 11/2005 |
| WO | 2006053039 A2 | 5/2006 |
| WO | 2006053082 | 5/2006 |
| WO | WO 2006053039 A2 * | 5/2006 |
| WO | 2006011440 | 11/2006 |
| WO | 2007134034 | 11/2007 |
| WO | 2007134038 | 11/2007 |
| WO | 2007147014 A2 | 12/2007 |
| WO | 2008034041 | 3/2008 |
| WO | 2008073942 | 6/2008 |
| WO | 2008091588 | 7/2008 |
| WO | 2008091592 | 7/2008 |

OTHER PUBLICATIONS

Acheson et al., "Transformations involving the Pyrrolidine Ring of Nicotine," J Chem Soc (1980) 1:579-585.

Arneric et al., "Cholinergic channel modulators as a novel therapeutic strategy for Alzheimer's disease," Exp Opin Invest Drugs (1996) 5(1):79-100.

Arneric et al., "Preclinical Pharmacology of ABT-418: A Prototypical Cholinergic Channel Activator for the Potential Treatment of Alzheimer's Disease," CNS Drug Rev (1995) 1(1):1-26.

Ashimori et al., "Novel 1, 4-Dihydropyride Calcium Antagonists. I. Synthesis and Hypotensive Activity of 4-(Substittuted Pyridyl)-1,4-dihydropyridine Derivatives" Chem. Pharm Bull (1990) 38(9):2446-2458.

Bannon et al., "Broad-Spectrum, Non-Opioid Analgesic Activity by Selective Modulation of Neuronal Nicotinic Acetylcholine Receptors," Science (1998) 279:77-81.

Batkowski, Rocz Chem (1967) 41:729-741.

Bencherif et al., "Targeting Neuronal Nicotinic Receptors: a Path to New Therapies," Current Drug Targets (2002) 1 (4):349-357.

Bencherif et al., "RJR-2403: A Nicotinic Agonist with CNS Selectivity I: In Vitro characterization," J Pharmacol Exper Therapeutics (1996) 279(3):1413-1421.

Borch "Reductive Amination with Sodium Cyanoborohydride: N, N-Dimethylcyclohexyl," Org Syn (1974) 52:124-127.

Brioni et al., "The harmacology of (–)-Nicotine and Novel Cholinergic channel Modulators," Adv Pharmacol (1997) 37:153-214.

Cai et al., "5-(N-Oxyaza-7-substituted-1,4-dihydroquinoxaline-2,3-diones: Novel, Systemically Active and Broad Spectrum an," J Med Chem (1997) 40(22):3679-3686.

Cheng et al., "Relationship Between the Inhibition Constant (KI) and the Concentration of Inhibitor which Causes 50 Per Cent inhibition (I50) of an Enzymatic Reaction," (1973) Biochem Pharmacol (1973) 22(23):3099-3108.

Chiari et al., "Sex Differences in Cholinergic Analgesia I: A Supplemental Nicotinic Mechanism in Normal Females," (1999) Anesthesiology 91(5):1447-1454.

Comins et al., "Lithiation of Methoxypyridines Directed by beta-Amino Alkoxides," (1990) J Org Chem 91(5):69-73.

Dallacker et al., "," Naturforsch (1979) 34b:1729-1736.

Damaj et al., "Analgesic Activity of Metanicotine, A Selective Nicotinic Agonist," Neuroscience (1997) 23:669.

Damaj et al., "Antinociceptive and Pharmacological Effects of Metanicotine, a Selective Nicotinic Agonist," J Pharmacol Exp Ther (1999) 291(1):390-398.

Decina et al., "Cigarette Smoking and Neuroleptic-Induced Parkinsonism," Biol Psychiatry (1990) 28(6):502-508.

Dubey et al., "Synthesis & Spectra of 2-Alkyl--& 6-Bromo-2-alkyl-1H-imidazo[b]pyridines," Indian J Chem (1978) 16B (6):531-533.

Dwoskin et al., "Recent developments in neuronal nicotinic acetylcholine receptor antagonists," Exp Opin Ther Patents (2000) 10(10):1561-1581.

Frank et al., "Palladium-Catalyzed Vinylic Substitution Reactions with Heterocyclic Bromides," J Org Chem (1978) 43 (15):2947-2949.

Frissen et al., "Ring-Transformations of Pyrimidines by Intramolecular Diels-Alder Reactions, Sythesis of Annelated Pyridines," Tetrahedron (1989) 45(3):803-812.

Gibson et al., "Principal Components Describing biological Activities and Molecular Diversity of Heterocyclic Aromatic Ring Fragments," J Med Chem (1996) 39:4065-4072.

Greco et al., "Synthese of Some Substituted Pyridylsydnones," J Heterocyclic Chem (1970) 7:761-766.

Hall et al., "Effects of Nicotine on the Release of 3H-Noradrenaline from the Hypothalamus," Biochemical Pharmacology (1972) 21:1829-1838.

Hamon "Neuropharmacology of anxiety: perspectives and prospects," TIPS (1994) 15:36-39.

Harsing et al., "Dopamine Efflux from Striatun After Chronic Nicotine: Evidence for Autoreceptor Desensitization," J Neurochem (1992) 59(1):48-54.

Hayes et al., Elimination of Dihydrogen from Collision-activated Alkoxide Negative Ions in the Gas Phase. An Ab inition and Isotope Effect Study, J Chem Soc Chem Commun (1984) 21:1431-1432.

Hertog et al., "The Reactivity of Bromine Atoms in Brominated Pyridines," Recl Tray Chim Pays-Bas (1948) 67 (7!8):377-379.

Hery et al., "Control of the release of newly synthetized 3H-5-Hydroxytryptamine by Nicotinic and Muscarinic Receptors in Rat Hypothalamic Slices," Naunyn-Schmiedeberg's Arch Pharmacol (1977) 296:91-97.

Holladay et al., "Neuronal Nicotinic Acetylcholine Receptors as Targets for Drug Discovery," J Med Chem (1997) 40 (26):4169-4194.

Hoyer et al., "Partial agonists, full agonists, antagonists: dilemmas of definition," TIPS Reviews (1993) 14:270-275.

Hughes et al., "S 40 Nicitine and Neuropsychiatric Disorders," Session 6, in International Symposium on Nicotine: The Effects of Nicotine on Biological Systems II, (Birkhauser Verlag Publishers, 1994).

Ishihara et al., "Zinc Bromide Promoted Allylatin of Aluminum Acetals Derived from Perfluoro Carboxylic Acid Esters and Diisobutylaluminum Hybride," Tetrahedron Letters (1993) 34(36):5777-5780.

Kalivretenos et al., "Synthesis of Beta-Resocylic Macrolides via Organopalladium Chemistry Application to the Total Synthesis of (S)-Zearalenone," J Org Chem (1991) 56:2883-2894.

Koch et al., "Chemistry of 3-Hydroxypyridine Part 2: Synthesis of 5,6 -Dihalo-3-hydroxypyriines," Synthesis (1990) 499-501.

Kubota et al., "Facile Synthesis of Beta-Trifluoromethlated Alcohols from Trifluoroacetaldehyde Ethyl Hemiacetal," Tetrahedron Letters (1992) 33(10):1351-1354.

Kuhler et al., "Structure-Activity Relationship of Omeprazole and Analogues as Helicobacter pylorie Urease Inhimitors," J Med Chem (1995) 38:4906-4916.

LaForge "The preparation and properties of some new derivatives of pyridine," J Am Chem Soc (1928) 50:2477-2483.

Lavand'homme et al., "Sex Differences in Cholinergic Analgesia II: differing Mechanisms in Two Models of Allodynia," Anesthesiology (1999) 91(5):1455-1461.

Levin et al., "Nicotinic treatment for cognitive dysfunction," Current Drug Targets: CNS and Neurological Disorders (2002) 1(4):423-431.

Lippiello et al., "RJR-2403: a nicotinic agonist with CNS selectivity II. In vivo characterization," J Pharmacol Exp Ther (1996) 279(3):1422-1429.

Loffer et al., "[Uber die bildung des i-nicotins aus N-methyl-b-pyridyl-butyl-amin (dihydrometanicotin)]," Chem Ber (1909) 42:3431-3438.

Malek et al., "Palladium-catalyzed synthesis of cinnamylamines," J Org Chem (1982) 47:5395-5397.

Michael et al., "Synthesis of functionalized cyclopentanes, cyclohexanes and cycloheptanes by a silicon-induced domino reaction," Liebigs Ann (1996) 11:1811-1821.

Morisawa et al., "Modification at 5-position of 4-deoxypyridoxol and alpha4-norpyridoxol," Agr Biol Chem (1975) 39 (6):1275-1281.

Onaivi et al., "Chronic nicotine reverses age-associated increases in tail-flick latency and anxiety in rats," Life Sciences (1993) 54(3):193-202.

O'Neill et al., "The role of neuronal nicotinic acetylcholine receptors in acute and chronic neurodegeneration," Current Drug Targets: CNS and Neurological Disorders (2002) 1(4):399-411.

Paulder et al., "1,2,4-Triazines. III. A convenient synthesis of 1,2,4-triazines and their covalent hydration," J Heterocyclic Chem (1970) 7:767-771.

Pomerleau et al., "The effects of cigarette smoking on pain and anxiety," Addictive Behaviors (1984) 9(3):265-271.

Pullan et al., "Transdermal nicotine for active ulcerative colitis," New England J Med (1994) 330(12):811-815.

Rapier et al., "Stereoselective nicotine-induced release of dopamine from striatal synaptosomes: concentration dependence and repetitive stimulation," J Neurochem (1988) 50(4):1123-1130.

Rondahl "Synthetic analogues of nicotine VI 1,2. Nicotine substituted in the 5-position," Acta Pharmaceutica Suecica (1977) 14(2):113-118.

Rowell et al., "Nicotinic stimulation of [3H]acetylcholine release from mouse cerebral cortical synaptosomes," J Neurochem (1984) 43(6):1593-1598.

Sanberg et al., "Nicotine potentiation of haloperidol-induced catalepsy: striatal mechanisms," Pharmacol Biochem & Behavior (1993) 46(2):303-307.

Sandor et al., "Effect of nicotine on dopaminergic-cholinergic interaction in the striatum," Brain Res (1991) 567 (2):313-316.

Sjak-Shie et al., "Effects of chronic nicotine and pilocarpine administration on neocortical neuronal density and [3H] GABA uptake in nucleus basalis lesioned rats," Brain Res (1993) 624:295-298.

Schmitt et al., "Chapter 5. Targeting nicotinic acetylcholine receptors: advances in molecular design and therapies," Ann Rep Med Chem (2000) 35:41-51.

Taylor et al., "Intramolecular diels-alder reactions of 1,2,4-triazines. A general synthesis of furo[2,3- ]pyridines, 2,3- dihydropyrano[2,3- ]pyridines, and pyrrolo[2,3- ]pyridines," Tetrahedron (1987) 43(21):5145-5158.

Toth et al., "Effect of nicotine of extracellular levels of neurotransmitters assessed by microdialysis in various brain regions: role of glutamic acid," Neurochem Res (1992) 17(3):265-270.

Tripathi et al., "Nicotine-induced antinociception in rats and mice: correlation with nicotine brain levels," J Pharmacol Exp Ther (1982) 221(1):91-96.

Viaud et al., "Synthesis of 6-substituted 2-phenyloxazolo-[4,5-b]pyridines," Heterocycles (1995) 41(12):2799-2809.

Vizi et al., "Acetylcholine release from guinea-pig ileum by parasympathetic ganglion stimulants and gastrin-like polypeptides," Br J Pharmac (1973) 47(4):765-777.

Wagner et al., "Does smoking reduce the risk of neuroleptic parkinsonoids?" Pharmacopsychiat (1988) 21:302-303.

Williams et al., "Neuronal nicotinic acetylcholine receptors," Drug News Perspec (1994) 7(4):205-223.

Yoshikawa et al., "Synthesis of 3-pyridinols. II. Reaction of 4-methyloxazole with dienophiles," Chem Pharm Bull (1965) 13(7):873-878.

Bibliographic printout from Dialog research company (corresponding to Japanese Patent No. 70012732).

Office Action dated Jan. 7, 2008 copending U.S. Appl. No. 11/270,018.

Notice of Allowance dated Apr. 8, 2008 copending U.S. Appl. No. 11/270,753.

Geerts "Ispronicline Targacept," Current Opinion in Investigational Drugs (2006) 7(1):60-69.

Buccafusco "Neuronal nicotinic receptor subtypes: defining therapeutic targets," Molecular Interventions (2004) 4 (5):285-295.

Haberman "Nicotinic receptor agonists for treating diseases of cognitive dysfunction," Spectrum (2007) pp. 11-1 to 11-19.

Bastin, et al, Salt Selection and Optimization for Pharmaceutical New Chemical Entities, Organic Process Research and Development, 2000; 4(5):427-435.

Levin, et al., Nicotine-Haloperidoal Interactions and Cognitive Performance in Schizophrenics, Neuropsychopharmacology, 1996;15(5):429-436.

Ichikawa, et al., Atypical antipsychotic drugs, quetiapine, iloperidone, and melperone, preferentially increase dopamine and acetylcholine release in rat medial prefrontal cortex: role of 5-HT1A receptor agonism, Brain Research (2002) 956:349-357.

Shoemaker, et al., Quetiapine produces a prolonged reversal of the sensorimotor gating-disruptive effects of basolateral amygdala lesions in rats, Behavioral Neuroscience (2003) 117(1):136-143.

Notice of allowance for co-pending U.S. Appl. No. 11/270,018 dated Aug. 4, 2008.

Office Action for co-pending U.S. Appl. No. 11/855,175 dated Nov. 13, 2008.

Supplemental Notice of Allowability for co-pending U.S. Appl. No. 11/270,753 dated May 16, 2008.

Notice of Allowance for co-pending U.S. Appl. No. 11/270,753 dated Oct. 24, 2008.

Letchworth et al., "Tc-1734: an orally active neuronal nicotinic receptor modulator with long-lasting cognitive effects, anti-depressant effects, and neuroprotective activity," Society for Neuroscience (2003) Abstract.

Notice of Allowance dated May 12, 2011 copending U.S. Appl. No. 12/299,925.

Canney et al., "Characterization of ethyl (3-quinuclidinyl) acetate (EQA) as a ligand for acetylcholine receptors," Life Sciences (1998) 63(24):PL329-PL336.

Non-final office action dated Jan. 14, 2011 copending U.S. Appl. No. 12/264,288.

Berge et al., "Pharmaceutical Salts," (1977) J Pharma Sci 66(1):1-19.

Non-final office action dated Dec. 15, 2010 copending U.S. Appl. No. 12/299,925.

* cited by examiner

POLYMORPH FORMS OF (2S)-(4E)-N-METHYL-5-[3-(5-ISOPROPDXY-PYRIDIN)YL]-4-PENTEN-2-AMINE

This application claims benefit of U.S. Provisional Patent Application No. 60/746,821, filed May 9, 2006.

FIELD OF THE INVENTION

The present invention relates to novel polymorph forms of (2S)-(4E)-N-methyl-5-[3-(5-isopropoxypyridin)yl]-4-penten-2-amine p-hydroxybenzoate, as well as pharmaceutical compositions including the polymorph forms. The present invention also relates to methods for treating a wide variety of conditions and disorders, and particularly conditions and disorders associated with dysfunction of the central and autonomic nervous systems, using the novel polymorph forms.

BACKGROUND OF THE INVENTION

In the formulation of drug compositions, it is important for the drug substance to be in a form in which it can be conveniently handled and processed. This is of importance, not only from the point of view of obtaining a commercially-viable manufacturing process, but also from the point of view of subsequent manufacture of pharmaceutical compositions comprising the active compound.

Further, in the manufacture of drug compositions, it is important that a reliable, reproducible and constant plasma concentration profile of drug is provided following administration to a patient.

Chemical stability, solid state stability, and "shelf life" of the active ingredients are also very important factors. The drug substance, and compositions containing it, should preferably be capable of being effectively stored over appreciable periods of time, without exhibiting a significant change in the active component's physico-chemical characteristics (e.g. its chemical composition, density, hygroscopicity and solubility).

Moreover, it is also important to be able to provide drugs in a form, that are as chemically pure as possible.

The skilled person will appreciate that, typically, if a drug can be readily obtained in a stable form, such as a stable crystalline form, advantages may be provided, in terms of ease of handling, ease of preparation of suitable pharmaceutical compositions, and a more reliable solubility profile.

The compound (2S)-(4E)-N-methyl-5-[3-(5-isopropoxypyridin)yl]-4-penten-2-amine is known to provide benefits in the area of the treatment and/or prevention of central nervous system disorders. The compound, its synthesis, and its use in methods of medical treatment, is described, for example, in PCT WO 99/65876 to Caldwell et al. and in U.S. application Ser. No. 11/270,018, the contents of which are hereby incorporated by reference in their entirety.

SUMMARY OF THE INVENTION

The present invention relates to two polymorphic forms of (2S)-(4E)-N-methyl-5-[3-(5-isopropoxypyridin)yl]-4-penten-2-amine p-hydroxybenzoate (hereinafter referred to as Polymorphs A and B), methods of preparing the polymorph forms, and pharmaceutical compositions including the polymorph forms. Polymorphs A and B of the p-hydroxybenzoate salt of (2S)-(4E)-N-methyl-5-[3-(5-isopropoxypyridin)yl]-4-penten-2-amine are specifically disclosed.

The present invention also relates to methods for treating and/or preventing a wide variety of conditions or disorders, and particularly those disorders characterized by dysfunction of nicotinic cholinergic neurotransmission including disorders involving neuromodulation of neurotransmitter release, such as dopamine release. The present invention also relates to methods for treating and/or preventing disorders, such as central nervous system (CNS) disorders, which are characterized by an alteration in normal neurotransmitter release, and also for treating certain conditions (e.g., alleviating pain). The methods involve administering to a subject an effective amount of the novel polymorph forms, or pharmaceutical compositions including such polymorph forms.

The polymorph forms can be provided in the form of a pharmaceutical composition that includes an effective amount of the one of the polymorph forms or mixtures thereof, as described herein. The pharmaceutical compositions incorporating the polymorph form(s) of (2S)-(4E)-N-methyl-5-[3-(5-isopropoxypyridin)yl]-4-penten-2-amine p-hydroxybenzoate, which, when employed in effective amounts, interacts with relevant nicotinic receptor sites of a subject, and hence has acts as a therapeutic agent to treat and prevent a wide variety of conditions and disorders, particularly those disorders characterized by an alteration in normal neurotransmitter release.

The pharmaceutical compositions are believed to be safe and effective with regard to prevention and treatment of a wide variety of conditions and disorders as described below.

The foregoing and other aspects of the present invention are explained in detail in the detailed description and examples set forth below.

DETAILED DESCRIPTION

Two polymorph forms of (2S)-(4E)-N-methyl-5-[3-(5-isopropoxypyridin)yl]-4-penten-2-amine p-hydroxybenzoate, pharmaceutical compositions, methods of preparing these forms, and methods of treatment and/or prevention using these forms, are described in detail below.

According to a further aspect of the invention there is provided a salt of the invention in substantially crystalline form. Although we have found that it is possible to produce salt forms of the invention in forms which are greater than 80% crystalline, by "substantially crystalline" we include greater than 20%, preferably greater than 30%, and more preferably greater than 40% (e.g. greater than any of 50, 60, 70, 80 or 90%) crystalline.

According to a further aspect of the invention there is also provided a salt forms of the invention in partially crystalline form. By "partially crystalline" we include 5% or between 5% and 20% crystalline. The degree (%) of crystallinity may be determined by the skilled person using X-ray powder diffraction (XRPD). Other techniques, such as solid state NMR, FT-IR, Raman spectroscopy, differential scanning calorimetry (DSC) and microcalorimetry, may also be used.

The term "stability" as defined herein includes chemical stability and solid state stability. By "chemical stability", we include that it may be possible to store salt forms of the invention in an isolated form, or in the form of a composition in which it is provided in admixture with pharmaceutically acceptable carriers, diluents or adjuvants (e.g. in an oral dosage form, such as a tablet, capsule etc.), under normal storage conditions, with an insignificant degree of chemical degradation or decomposition. By "solid state stability", we include that it may be possible to store salt forms of the invention in an isolated solid form, or in the form of a solid composition in which it is provided in admixture with pharmaceutically acceptable carriers, diluents or adjuvants (e.g. in an oral dosage form, such as a tablet, capsule etc.), under normal storage conditions, with an insignificant degree of solid state transformation (e.g. crystallisation, recrystallisation, solid state phase transition, hydration, dehydration, solvatisation or desolvatisation). Examples of "normal storage conditions" include temperatures of between minus 80 and plus 50° C. (preferably between 0 and 40° C. and more preferably room temperatures, such as 15 to 30° C.), pressures of between 0.1 and 2 bars (preferably at atmospheric pressure), relative humidities of between 5 and 95% (preferably 10 to 60%), and/or exposure to 460 lux of UV/visible light, for prolonged periods (i.e. greater than or equal to six months). Under such conditions, salt forms of the invention may be found to be less than 15%, more preferably less than 10%, and especially less than 5%, chemically degraded/decomposed, or solid state transformed, as appropriate. The skilled person will appreciate that the above-mentioned upper and lower limits for temperature, pressure and relative humidity represent extremes of normal storage conditions, and that certain combinations of these extremes will not be experienced during normal storage (e.g. a temperature of 50° C. and a pressure of 0.1 bar).

I. (2S)-(4E)-N-methyl-5-[3-(5-isopropoxypyridin) yl]-4-penten-2-amine

The compounds described herein are polymorphs of (2S)-(4E)-N-methyl-5-[3-(5-isopropoxypyridin)yl]-4-penten-2-amine p-hydroxybenzoate, which has the formula:

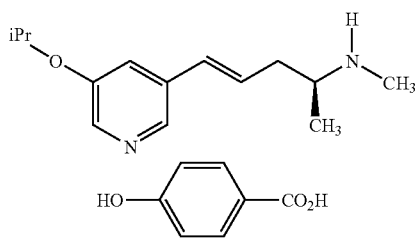

The manner in which the (2S)-(4E)-N-methyl-5-[3-(5-isopropoxypyridin)yl]-4-penten-2-amine p-hydroxybenzoate, in its polymorphic forms, can be prepared can vary. Approaches for preparing (2S)-(4E)-N-methyl-5-[3-(5-isopropoxypyridin)yl]-4-penten-2-amine are described, for example, in PCT WO 99/65876 to Caldwell et al. and in U.S. application Ser. No. 11/270,018, pertinent portions of which are summarized below.

One synthetic approach involves a convergent synthesis, in which the side chain, (2S)-N-methyl-N-(tert-butoxycarbonyl)-4-penten-2-amine is coupled with the 3-substituted 5-halo-substituted pyridine, 5-bromo-3-isopropoxypyridine, under Heck reaction conditions, followed by removal of the tert-butoxycarbonyl protecting group. Typically, the types of procedures set forth in W. C. Frank et al., *J. Org. Chem.* 43: 2947 (1978) and N. J. Malek et al., *J. Org. Chem.* 47: 5395 (1982) involving a palladium-catalyzed coupling of an olefin and an aromatic halide are used. The required (2S)-N-methyl-N-(tert-butoxycarbonyl)-4-penten-2-amine can be synthesized as follows: (i) (2R)-4-Penten-2-ol can be prepared from (R)-(+)-propylene oxide, according to procedures set forth in A. Kalivretenos, J. K. Stille, and L. S. Hegedus, *J. Org. Chem.* 56: 2883 (1991), and then treated with p-toluenesulfonyl chloride in pyridine to yield (2R)-4-penten-2-ol p-toluenesulfonate. (ii) The resulting tosylate can be heated with 20 molar equivalents of methylamine (as a 40% aqueous solution) in dimethylformamide to yield (2S)-N-methyl-4-penten-2-amine. (iii) The resulting amine can be allowed to react with di-tert-butyl dicarbonate in ether to yield the side chain, (2S)-N-methyl-N-(tert-butoxycarbonyl)-4-penten-2-amine.

The halo-substituted pyridine, (e.g., 5-bromo-3-isopropoxypyridine) can be synthesized by two different routes. In one preparation, 3,5-dibromopyridine is heated at 140° C. for 14 hours with 2 molar equivalents of potassium isopropoxide in dry isopropanol in the presence of copper powder (5%, w/w of the 3,5-dibromopyridine) in a sealed glass tube to yield 5-bromo-3-isopropoxypyridine. A second preparation of 5-bromo-3-isopropoxypyridine from 5-bromonicotinic acid can be performed as follows: (i) 5-Bromonicotinic acid is converted to 5-bromonicotinamide by treatment with thionyl chloride, followed by reaction of the intermediate acid chloride with aqueous ammonia. (ii) The resulting 5-bromonicotinamide, previously described by C. V. Greco et al., *J Heteocyclic Chem.* 7(4): 761 (1970), is subjected to Hofmann degradation by treatment with sodium hydroxide and a 70% solution of calcium hypochlorite. (iii) The resulting 3-amino-5-bromopyridine, previously described by C. V. Greco et al., *J Heteocyclic Chem.* 7(4): 761 (1970), can be converted to 5-bromo-3-isopropoxypyridine by diazotization with isoamyl nitrite under acidic conditions, followed by treatment of the intermediate diazonium salt with isopropanol to yield 5-bromo-3-isopropoxypyridine. The palladium-catalyzed coupling of 5-bromo-3-isopropoxypyridine and (2S)-N-methyl-N-(tert-butoxycarbonyl)-4-penten-2-amine is carried out in acetonitrile-triethylamine (2:1, v,v) using a catalyst consisting of 1 mole % palladium(II) acetate and 4 mole % tri-o-tolylphosphine. The reaction can be carried out by heating the components at 80° C. for 20 hours to yield (2S)-(4E)-N-methyl-N-(tert-butoxycarbonyl)-5-[3-(5-isopropoxypyridin)yl]-4-penten-2-amine. Removal of the tert-butoxycarbonyl protecting group can be accomplished by treatment with 30 molar equivalents of trifluoroacetic acid in anisole at 0° C. to afford (2S)-(4E)-N-methyl-5-[3-(5-isopropoxypyridin)yl]-4-penten-2-amine.

II. p-Hydroxybenzoate Salt of (2S)-(4E)-N-methyl-5-[3-(5-isopropoxypyridin)yl]-4-penten-2-amine Typically the p-hydroxybenzoate salt of (2S)-(4E)-N-methyl-5-[3-(5-isopropoxypyridin)yl]-4-penten-2-amine is prepared by reacting about one equivalent of p-hydroxybenzoic acid with (2S)-(4E)-N-methyl-5-[3-(5-isopropoxypyridin)yl]-4-penten-2-amine in some suitable solvent, such as methanol, ethanol, isopropyl alcohol, acetone, ethyl acetate, or acetonitrile. Sometimes water is present in the reaction mixture. These procedures are described in detail in U.S. application Ser. No. 11/270,018.

III. Polymorphs of (2S)-(4E)-N-methyl-5-[3-(5-isopropoxypyridin)yl]-4-penten-2-amine-hydroxybenzoate salt Polymorphs A and B of the p-hydroxybenzoate salt of (2S)-(4E)-N-methyl-5-[3-(5-isopropoxypyridin)yl]-4-penten-2-amine are disclosed.

The polymorph forms of (2S)-(4E)-N-methyl-5-[3-(5-isopropoxypyridin)yl]-4-penten-2-amine p-hydroxybenzoate are prepared by recrystallizing the salt in various solvents. Representative procedures are given in the Examples. A variety of solvents may be utilized in the formation of polymorphs A and B. Appropriate choice of solvent(s) for recrystallization provides either polymorph A or B in relatively pure form (i.e., greater than 95% polymorph A or greater than 95% polymorph B). The invention thus provides both polymorph A and polymorph B in relatively pure form (greater than 95% polymorphic purity).

Depending upon the manner by which the polymorphs described herein are formed, the polymorph can have crystal structures that occlude solvents that are present during polymorph formation. Thus, the polymorph can occur as hydrates and other solvates of varying stoichiometry of solvent relative to the (2S)-(4E)-N-methyl-5-[3-(5-isopropoxypyridin)yl]-4-penten-2-amine p-hydroxybenzoate. Representative solvents that can be used to prepare and/or recrystallize the polymorphs include, without limitation, ethanol, methanol, isopropyl alcohol, acetone, ethyl acetate, and/or acetonitrile.

A series of solid-state techniques can be used to evaluate two polymorphic forms of the p-hydroxybenzoate salt of (2S)-(4E)-N-methyl-5-[3-(5-isopropoxypyridin)yl]-4-penten-2-amine. X-ray Powder Diffraction (XRPD) was used to evaluate the unique crystalline phase and structural characteristics of the polymorphs and mixtures. Differential Scanning Calorimetry (DSC) may also be performed.

One aspect of the invention relates to a mixture of polymorph A and polymorph B. In one embodiment the ratio of polymorph A to B is 40 to 60. In another embodiment the ratio is 30 to 70. In a further embodiment the ratio is 20 to 80. In yet another embodiment the ratio is 10 to 90. In yet another embodiment the ratio is 5 to 95. Likewise, in one embodiment the ratio of polymorph B to A is 40 to 60. In another embodiment the ratio is 30 to 70. In a further embodiment the ratio is 20 to 80. In yet another embodiment the ratio is 10 to 90. In yet another embodiment the ratio is 5 to 95. Thus, the invention also provides mixtures of polymorphs A and B in ratios ranging from 5:95 to 95:5.

IV. Methods of Treatment

The salt forms described herein can be used in methods for preventing and/or treating a condition or disorder in a subject susceptible to such a condition or disorder. For example, an effective amount of a compound effective for providing some degree of prevention of the progression of a CNS disorder (i.e., provide protective effects), amelioration of the symptoms of a CNS disorder, and amelioration of the reoccurrence of a CNS disorder, can be administered to a patient in need thereof.

The compounds can be used to treat and/or prevent those types of conditions and disorders for which other types of nicotinic compounds have been proposed as therapeutics. See, for example, Williams et al. DN&P 7(4):205-227 (1994), Arneric et al., CNS Drug Rev. 1(1):1-26 (1995), Arneric et al., Exp. Opin. Invest. Drugs 5(1):79-100 (1996), Bencherif et al., JPET 279:1413 (1996), Lippiello et al., JPET 279:1422 (1996), Damaj et al., Neuroscience (1997), Holladay et al., J. Med. Chem. 40(28): 4169-4194 (1997), Bannon et al., Science 279: 77-80 (1998), PCT WO 94/08992, PCT WO 96/31475, and U.S. Pat. No. 5,583,140 to Bencherif et al., U.S. Pat. No. 5,597,919 to Dull et al., and U.S. Pat. No. 5,604,231 to Smith et al the disclosures of which are incorporated herein by reference in their entirety.

The compounds modulate nicotinic receptors in the patient's brain. As such, such compounds have the ability to express nicotinic pharmacology, and in particular, to act as nicotinic partial agonists.

Receptor binding constants provide a measure of the ability of the compound to bind to half of the relevant receptor sites of certain brain cells of the patient. See, Cheng, et al., Biochem. Pharmacol. 22:3099 (1973). The (2S)-(4E)-N-methyl-5-[3-(5-isopropoxypyridin)yl]-4-penten-2-amine compound used to prepare the salt forms has extremely high affinity for the relevant receptors, with a binding affinity in the low nM range.

The compounds have the ability to demonstrate a nicotinic function by effectively modulating neurotransmitter secretion from neurons. As such, such compounds have the ability to affect relevant the release of acetylcholine, dopamine, and other neurotransmitters by neurons.

The compounds, when employed in effective amounts in accordance with the methods described herein, are selective to certain relevant nicotinic receptors, but do not cause significant activation of receptors associated with undesirable side effects at concentrations at least greater than those required for modulation of CNS neuronal activity. The selectivity of the compounds against those ganglia-type receptors responsible for cardiovascular side effects is demonstrated by a lack of the ability of those compounds to activate nicotinic function of adrenal chromaffin tissue at concentrations greater than those required for modulation of CNS neuronal activity.

Thus, administration of the compounds provides a therapeutic window in which treatment of certain CNS disorders is provided, and certain side effects are avoided. That is, an effective dose of the compound is sufficient to provide the desired effects upon the CNS, but is insufficient (i.e., is not at a high enough level) to provide undesirable side effects. The pharmaceutical compositions are useful in the treatment of a variety of CNS disorders, including neurodegenerative disorders, neuropsychiatric disorders, neurologic disorders, and addictions. The pharmaceutical compositions can be used to treat cognitive deficits (age-related and otherwise), attentional disorders and dementias (including those due to infectious agents or metabolic disturbances); to provide neuroprotection; to treat convulsions and multiple cerebral infarcts; to treat mood disorders, compulsions and addictive behaviors; to provide analgesia; and to control inflammation (such as mediated by cytokines and nuclear factor kappa B) and treat inflammatory disorders. Among the disorders, diseases and conditions, that pharmaceutical compositions of the present invention can be used to treat, are: age-associated memory impairment, mild cognitive impairment, pre-senile dementia (early onset Alzheimer's disease), senile dementia (dementia of the Alzheimer's type), Lewy body dementia, vascular dementia, Alzheimer's disease, stroke, AIDS dementia complex, attention deficit disorder, attention deficit hyperactivity disorder, dyslexia, schizophrenia, schizophreniform disorder, schizoaffective disorder, Parkinsonism including Parkinson's disease, Pick's disease, Huntington's chorea, tardive dyskinesia, hyperkinesia, progressive supranuclear palsy, Creutzfeld-Jakob disease, multiple sclerosis, amyotrophic lateral sclerosis, epilepsy, depression, panic disorders, bipolar disorders, generalized anxiety disorder, obsessive compulsive disorder, rage outbursts, Tourette's syndrome, autism, drug and alcohol addiction, tobacco addiction, obesity, acute pain, neuropathic pain, inflammatory pain, ulcerative colitis, irritable bowel syndrome, cachexia, osteoarthritis, psoriasis, rheumatoid arthritis, endotoxaemia, sepsis, asthma, atherosclerosis and idiopathic pulmonary fibrosis.

Thus, the present invention relates to the salt forms mentioned above for use in therapy. The present invention further relates to the use of said salt forms, in the manufacture of a medicament for treatment of a central nervous system disorder. Also provided is a method for treatment of a central nervous system disorder, comprising administering to a mammal in need of such treatment, a therapeutically effective amount of the salt forms of the present invention. Further provided is a method for treatment of disorders selected from the group consisting of age-associated memory impairment, mild cognitive impairment, pre-senile dementia (early onset Alzheimer's disease), senile dementia (dementia of the Alzheimer's type), Lewy body dementia, vascular dementia, Alzheimer's disease, stroke, AIDS dementia complex, attention deficit disorder, attention deficit hyperactivity disorder, dyslexia, schizophrenia, schizophreniform disorder, and schizoaffective disorder. Even further provided is a method for treatment of disorders selected from the group consisting of the treatment of mild to moderate dementia of the Alzheimer's type, attention deficit disorder, mild cognitive impairment and age associated memory impairment.

V. Pharmaceutical Compositions

According to one embodiment of the present invention there is provided a pharmaceutical composition comprising as active ingredient a therapeutically effective amount of salt forms of (2S)-(4E)-N-methyl-5-[3-(5-isopropoxypyridin)yl]-4-penten-2-amine, in association with one or more pharmaceutically acceptable diluents, excipients and/or inert carriers.

The manner in which the compositions are administered can vary. The compounds can be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); orally (e.g., in liquid form within a solvent such as an aqueous or non-aqueous liquid; intravenously (e.g., within a dextrose or saline solution); as an infusion or injection (e.g., as a suspension or as an emulsion in a pharmaceutically acceptable liquid or mixture of liquids); intrathecally; intracerebroventricularly; or transdermally (e.g., using a transdermal patch or by powder injection). Although it is possible to administer the compositions in the form of a bulk active chemical, it is preferred to present each compound in the form of a pharmaceutical composition for efficient and effective administration. Exemplary methods for administering such compounds will be apparent to the skilled artisan. For example, the compositions can be administered in the form of a tablet, a hard gelatin capsule or as a time release capsule. The administration of the pharmaceutical compositions described herein can be intermittent, or at a gradual, continuous, constant or controlled rate to a warm-blooded animal, (e.g., a mammal such as a mouse, rat, cat, rabbit, dog, pig, cow, or monkey); but advantageously is preferably administered to a human being. In addition, the time of day and the number of times per day that the pharmaceutical composition is administered can vary. Administration preferably is such that the active ingredients of the pharmaceutical composition interact with receptor sites within the body of the subject that effect the functioning of the CNS. More specifically, in treating a CNS disorder administration preferably is such so as to optimize the effect upon those relevant receptor subtypes, which have an effect upon the functioning of the CNS, while minimizing the effects upon muscle-type receptor subtypes.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder. Thus, when treating a CNS disorder, an effective amount of compound is an amount sufficient to pass across the blood-brain barrier of the subject, to bind to relevant receptor sites in the brain of the subject, and to modulate the activity of relevant nicotinic receptor subtypes (e.g., modulate neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the reoccurrence of the symptoms of the disorder.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to modulate relevant receptors to effect neurotransmitter (e.g., dopamine) release but the amount should be insufficient to induce effects on skeletal muscles and ganglia to any significant degree. The effective dose of compounds will of course differ from patient to patient but in general includes amounts starting where CNS effects or other desired therapeutic effects occur, but below the amount where muscular and ganglionic effects are observed.

Typically, the effective dose of compounds may require administering the compound in an amount of less than 5 mg/kg of patient weight. Often, the compounds may be administered in an amount from less than about 1 mg/kg patent weight to less than about 100 µg/kg of patient weight, and occasionally between from 10 µg/kg to less than 100 µg/kg of patient weight. The foregoing effective doses typically represent that amount administered as a single dose, or as one or more doses administered over a 24 hour period.

For human patients, the effective dose of the compounds may require administering the compound in an amount of at least about 1, but not more than about 1000, often not more than about 500 mg/24 hr./patient.

The compounds also can be administered in composition compositions that incorporate other ingredients, such as those types of ingredients that are useful in formulating a diagnostic composition. Compositions useful as diagnostics can be employed as set forth in U.S. Pat. No. 5,853,696 to Elmalch et al. and U.S. Pat. No. 5,969,144 to London et al., the contents of which are hereby incorporated by reference.

The compounds can also be formulated and/or administered in combination with other therapeutic compounds, such as those used in the treatment and or prevention of CNS disorders.

U.S. Provisional Application Ser. Nos. 60/746,808 and 60/746,821 are incorporated herein by reference in their entirety.

VI: EXPERIMENTALS

Example 1

Analysis of the Two Polymorphic Forms

The Polymorphs A and B were generated as described in Example 4.

A. Methods

X-ray powder diffraction analyses were performed using a PANalytical X'Pert Pro MPD diffractometer for 96 minutes from 1 to 60° 2θ with and without internal standard reference. The 2θ angles were corrected with regard to the standard values whereafter calculation into d-values (distance values) was done. The d-values may vary in the range ±2 on the last given decimal place. The sample preparation was performed according to standard methods, for example those described in Giacovazzo, C. et al (1995), Fundamentals of Crystallography, Oxford University Press; Jenkins, R. and Snyder, R. L.

(1996), Introduction to X-Ray Powder Diffractometry, John Wiley & Sons, New York; Bunn, C. W. (1948), Chemical Crystallography, Clarendon Press, London or Klug, H. P. & Alexander, L. E. (1974), X-ray Diffraction Procedures, John Wiley and Sons, New York.

The term "stability" as defined herein includes chemical stability and solid state stability.

By "chemical stability", we include that it may be possible to store salt forms of the invention in an isolated form, or in the form of a formulation in which it is provided in admixture with pharmaceutically acceptable carriers, diluents or adjuvants (e.g. in an oral dosage form, such as a tablet, capsule etc.), under normal storage conditions, with an insignificant degree of chemical degradation or decomposition.

By "solid state stability", we include that it may be possible to store salt forms of the invention in an isolated solid form, or in the form of a solid formulation in which it is provided in admixture with pharmaceutically acceptable carriers, diluents or adjuvants (e.g. in an oral dosage form, such as a tablet, capsule etc.), under normal storage conditions, with an insignificant degree of solid state transformation (e.g. crystallisation, recrystallisation, solid state phase transition, hydration, dehydration, solvatisation or desolvatisation).

Examples of "normal storage conditions" include temperatures of between minus 80 and plus 50° C. (preferably between 0 and 40° C. and more preferably room temperatures, such as 15 to 30° C.), pressures of between 0.1 and 2 bars (preferably at atmospheric pressure), relative humidities of between 5 and 95% (preferably 10 to 60%), and/or exposure to 460 lux of UV/visible light, for prolonged periods (i.e. greater than or equal to six months). Under such conditions, salt forms of the invention may be found to be less than 15%, more preferably less than 10%, and especially less than 5%, chemically degraded/decomposed, or solid state transformed, as appropriate. The skilled person will appreciate that the above-mentioned upper and lower limits for temperature, pressure and relative humidity represent extremes of normal storage conditions, and that certain combinations of these extremes will not be experienced during normal storage (e.g. a temperature of 50° C. and a pressure of 0.1 bar).

B. Results

Characterization of Polymorph A

A sample of pure Polymorph A was provided and tested "As-Is" by XRPD and shown in table 1.

Characterization of Polymorph B

A sample of pure Polymorph B was provided and tested "As-Is" by XRPD and shown in table 2.

The diffractability and preferred orientation of the two polymorphic forms were studied to determine if a method could be developed to minimize preferred orientation without increasing the amorphous content or altering the polymorphic form. This study involved attempts to randomize the sample presentation such that during data collection the powder pattern intensities remain somewhat constant. The crystals must be reduced to mimic the size of the other samples.

TABLE 1

Selected Unique X-Ray Powder Peaks for Polymorphs A.

| Corrected 2θ | distance (Å) | Rel intensity |
|---|---|---|
| 6.4 | 13.9 | vw |
| 7.6 | 11.7 | vs |
| 8.2 | 10.7 | w |
| 10.2 | 8.6 | vw |
| 14.7 | 6.0 | vw |
| 15.2 | 5.8 | s |

TABLE 1-continued

| | | |
|---|---|---|
| 16.4 | 5.4 | vw |
| 17.7 | 5.00 | vw |
| 18.1 | 4.89 | vw |
| 19.0 | 4.67 | w |
| 19.7 | 4.51 | m |
| 21.9 | 4.05 | vw |
| 22.2 | 4.01 | vw |
| 22.6 | 3.93 | vw |
| 22.8 | 3.89 | vw |
| 23.5 | 3.79 | m |
| 23.8 | 3.73 | vw |
| 24.2 | 3.68 | vw |
| 27.2 | 3.28 | w |
| 28.5 | 3.13 | vw |
| 30.6 | 2.92 | m |
| 34.9 | 2.57 | vw |
| 36.6 | 2.46 | vw |

Definitions used:

| % Relative intensity* | Definition |
|---|---|
| 100-50 | vs (very strong) |
| 50-10 | s (strong) |
| 10-2 | m (medium) |
| 2-0.7 | w (weak) |
| 0.7> | vw (very weak) |

*The relative intensities are derived from diffractograms measured with variable slits.

An embodiment of the invention is 2S)-(4E)-N-methyl-5-[3-(5-isopropoxypyridin)yl]-4-penten-2-amine p-hydroxybenzoate which exhibits at least the following characteristic X-ray powder diffraction peaks (expressed in degrees 2θ):

(1) 7.6 and 15.2 and 19.7, or (2) 6.4, 7.6, 15.2 and 19.7, or (3) 6.4, 7.6, 15.2, 19.7 and 30.6, or (4) 6.4, 7.6, 8.2, 10.2, 15.2, 19.7 and 30.6.

TABLE 2

Selected Unique X-Ray Powder Peaks for Polymorphs B.

| Corrected 2θ | distance (Å) | Rel intensity |
|---|---|---|
| 7.7 | 11.4 | s |
| 8.0 | 11.0 | vs |
| 9.6 | 9.2 | m |
| 10.5 | 8.4 | vw |
| 15.5 | 5.7 | m |
| 16.1 | 5.5 | s |
| 16.9 | 5.2 | m |
| 18.4 | 4.82 | w |
| 19.0 | 4.66 | w |
| 21.1 | 4.20 | vw |
| 21.9 | 4.05 | vw |
| 22.9 | 3.87 | vw |
| 23.5 | 3.79 | vw |
| 23.7 | 3.75 | vw |
| 27.0 | 3.30 | vw |

Definitions used:

| % Relative intensity* | Definition |
|---|---|
| 100-70 | vs (very strong) |
| 70-40 | s (strong) |
| 40-10 | m (medium) |
| 10-5 | w (weak) |
| 5> | vw (very weak) |

*The relative intensities are derived from diffractograms measured with variable slits.

An embodiment of the invention is (2S)-(4E)-N-methyl-5-[3-(5-isopropoxypyridin)yl]-4-penten-2-amine p-hydroxybenzoate which exhibits at least the following characteristic X-ray powder diffraction peaks (expressed in degrees 2θ):
1) 8.0, 9.6 and 16.1, or
2) 8.0, 9.6, 16.1 and 16.9, or
3) 8.0, 9.6, 16.1, 16.9 and 18.4, or
4) 8.0, 9.6, 10.5, 16.1, 16.9 and 18.4.

Example 2

Determination of Binding to Relevant Receptor Sites

Binding of the compounds to relevant receptor sites was determined in accordance with the techniques described in U.S. Pat. No. 6,953,855 to Mazurov et al. Inhibition constants (Ki values), reported in nM, were calculated from the $IC_{50}$ values using the method of Cheng et al., Biochem, Pharmacol. 22:3099 (1973). Low binding constants indicate that the compounds of the present invention exhibit good high affinity binding to certain CNS nicotinic receptors.

Example 3

Synthesis of (2S)-(4E)-N-methyl-5-[3-(5-isopropoxypyridin)yl]-4-penten-2-amine p-hydroxybenzoate (2S)-(4E)-N-Methyl-5-[3-(5-isopropoxypyridin)yl]-4-penten-2-amine p-hydroxybenzoate was prepared according to the procedures described in U.S. application Ser. No. 11/270,018.

Example 4

Preparation of Polymorphs A and B

Polymorph A:
A 10 g sample of (2S)-(4E)-N-methyl-5-[3-(5-isopropoxypyridin)yl]-4-penten-2-amine p-hydroxybenzoate was dissolved in refluxing acetone (81 ml) and 0.94 ml water. The solution was cooled to 48° C. and seeded with 100 mg of said compound. The resulting slurry was allowed to crystallize for 50 min at 48° C. This was then cooled down to 0° C. during 3 hr and left overnight at 0° C. The recrystallized material was collected by vacuum filtration, washed with 40 ml acetone and dried in a vacuum oven at 60° C., for 24 hr to give polymorph A.

Polymorph B:
A 10 g sample of (2S)-(4E)-N-methyl-5-[3-(5-isopropoxypyridin)yl]-4-penten-2-amine p-hydroxybenzoate was dissolved in refluxing acetone (81 ml) and 0.94 ml water. The solution was cooled to 48° C. and seeded with 100 mg of said compound, slurried in 1 ml acetone, and additionally washed with 1 ml acetone. The resulting slurry was allowed to crystallize for 50 min at 48° C. This was then cooled down to 0° C. during 3 hr and left overnight at 0° C. The recrystallized material was collected by vacuum filtration, washed with 40 ml acetone and dried in a vacuum oven at 60° C., for 72 hr to give polymorph B. This salt form was also dried up to 1 week in this last step.

The foregoing is illustrative of the present invention and is not to be construed as limiting thereof. The invention is defined by the following claims, with equivalents of the claims to be included therein.

The invention claimed is:

1. An isolated crystalline polymorph B of (2S)-(4E)-N-methyl-5-[3-(5-isopropoxypyridin)yl]-4-penten-2-amine p-hydroxybenzoate, exhibiting an X-ray powder diffraction pattern having characteristic peaks expressed in degrees)(2-θ°) at around 8.0, 9.6 and 16.1.

2. A mixture comprising polymorph A of (2S)-(4E)-N-methyl-5-[3-(5-isopropoxypyridin)yl]-4-penten-2-amine p-hydroxybenzoate, exhibiting an X-ray powder diffraction pattern having characteristic peaks expressed in degrees (2-θ°) at around 7.6 and 15.2 and 19.7; and polymorph B of (2S)-(4E)-N-methyl-5-[3-(5-isopropoxypyridin)yl]-4-penten-2-amine p-hydroxybenzoate, exhibiting an X-ray powder diffraction pattern having characteristic peaks expressed in degrees)(2-θ°) at around 8.0, 9.6 and 16.1, in ratios of 5:95 to 95:5.

3. An isolated polymorph B of (2S)-(4E)-N-methyl-5-[3-(5-isopropoxypyridin)yl]-4-penten-2-amine p-hydroxybenzoate of claim 1, wherein the polymorph is isolated by recrystallization from ethanol, methanol, isopropyl alcohol, ethyl acetate and/or acetonitrile.

4. An isolated crystalline polymorph B having an X-ray powder diffraction pattern substantially the same as that shown in table 2.

5. A pharmaceutical composition comprising as active ingredient a therapeutically effective amount of the polymorph according to any one of claim 1, 3, or 4, or the mixture of polymorphs of claim 2 in association with one or more pharmaceutically acceptable diluents, excipients and/or inert carriers.

6. A pharmaceutical composition comprising the compound of claim 1 in greater than 90% crystalline form.

* * * * *